(12) United States Patent
Gutschow et al.

(10) Patent No.: US 8,836,937 B2
(45) Date of Patent: Sep. 16, 2014

(54) ACTUATABLE VISUAL INSPECTION DEVICE

(71) Applicant: General Electric Company, Schenectady, NY (US)

(72) Inventors: Matthew Stephen Gutschow, San Jose, CA (US); Thomas James Batzinger, Burnt Hills, NY (US); Christopher Edward Thompson, Greenville, SC (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 13/680,919

(22) Filed: Nov. 19, 2012

(65) Prior Publication Data

US 2014/0139831 A1    May 22, 2014

(51) Int. Cl.
*G01N 21/01* (2006.01)
(52) U.S. Cl.
CPC ...................................... *G01N 21/01* (2013.01)
USPC ................................... 356/241.6; 356/241.1
(58) Field of Classification Search
CPC ..................................................... G01N 21/01
USPC ............... 356/241.1–241.6; 250/559.07, 347; 600/172, 141, 101, 114; 73/865.5, 73/865.8
See application file for complete search history.

(56) References Cited

U.S. PATENT DOCUMENTS

| | | | |
|---|---|---|---|
| 4,725,883 A * | 2/1988 | Clark et al. ..................... 348/84 |
| 4,735,501 A | 4/1988 | Ginsburgh et al. | |
| 4,790,624 A | 12/1988 | Van Hoye et al. | |
| 4,794,912 A | 1/1989 | Lia | |
| 4,846,573 A | 7/1989 | Taylor et al. | |
| 4,883,355 A | 11/1989 | Saghatchi et al. | |
| 4,934,786 A | 6/1990 | Krauter | |
| 4,941,454 A | 7/1990 | Wood et al. | |
| 4,991,957 A | 2/1991 | Sakamoto et al. | |
| 5,345,925 A | 9/1994 | Allred, III et al. | |
| 5,759,151 A | 6/1998 | Sturges | |
| 5,810,717 A * | 9/1998 | Maeda et al. ................. 600/151 |
| 6,162,171 A * | 12/2000 | Ng et al. ....................... 600/141 |
| 6,820,653 B1 * | 11/2004 | Schempf et al. ................ 138/98 |
| 7,164,476 B2 * | 1/2007 | Shima et al. ................ 356/241.1 |
| 7,171,279 B2 | 1/2007 | Buckingham et al. | |
| 7,312,454 B2 * | 12/2007 | Safai et al. ..................... 250/347 |
| 2007/0213590 A1 * | 9/2007 | Squicciarini .................. 600/172 |

* cited by examiner

*Primary Examiner* — Sang Nguyen
(74) *Attorney, Agent, or Firm* — Hoffman Warnick LLC; Ernest G. Cusick

(57) ABSTRACT

A visual inspection device for inspecting interior passages of a system is disclosed herein. In an embodiment, the visual inspection device includes a visual inspection tool and a tube having a lumen disposed therein, the visual inspection tool being disposed at a distal end of the tube. A plurality of actuators are disposed along an axial extent of an exterior of the tube, and a locomotor is disposed on an exterior of the tube. A locator for tracking a location of the visual inspection tool is also provided as part of the visual inspection device.

18 Claims, 8 Drawing Sheets

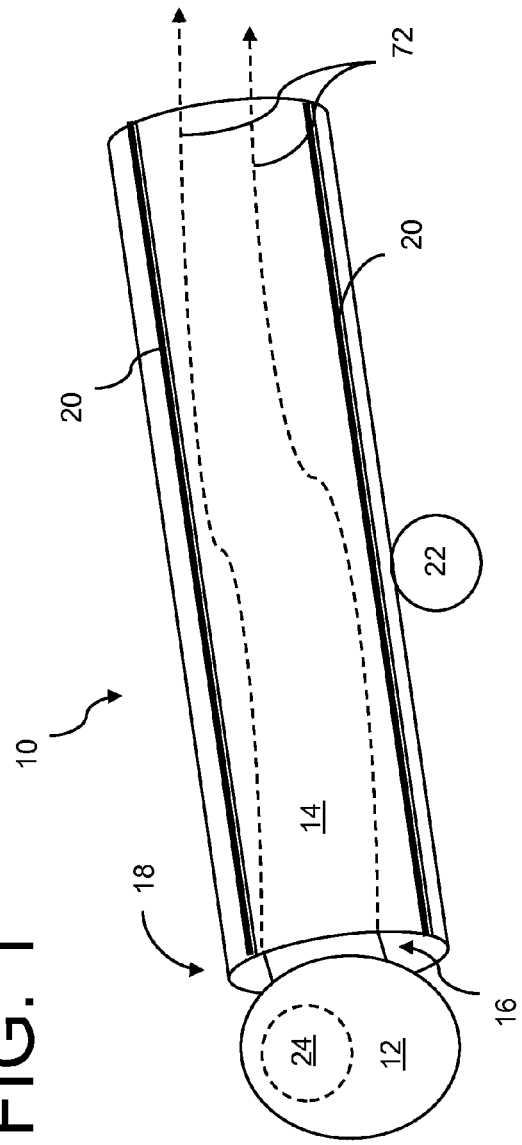
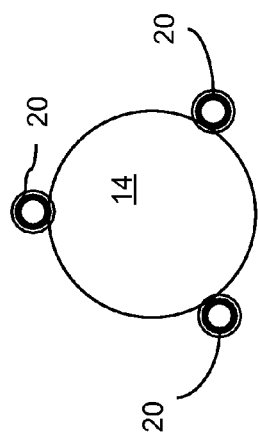
FIG. 1
FIG. 2

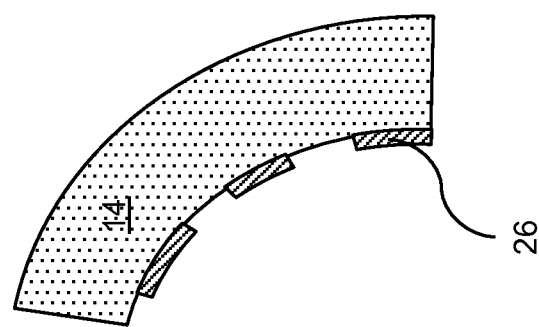
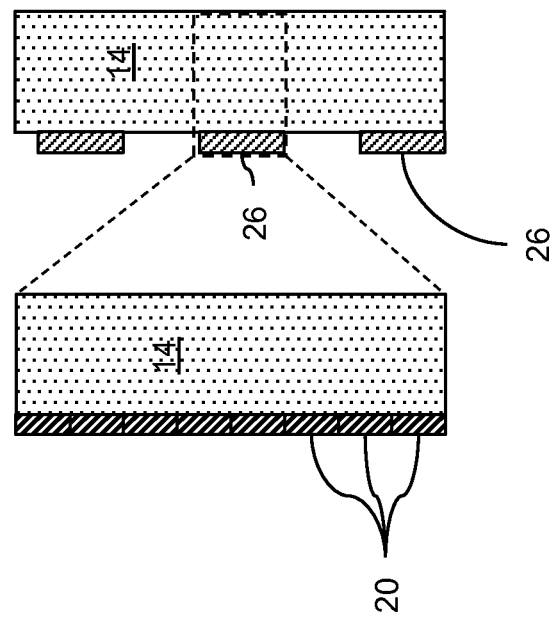

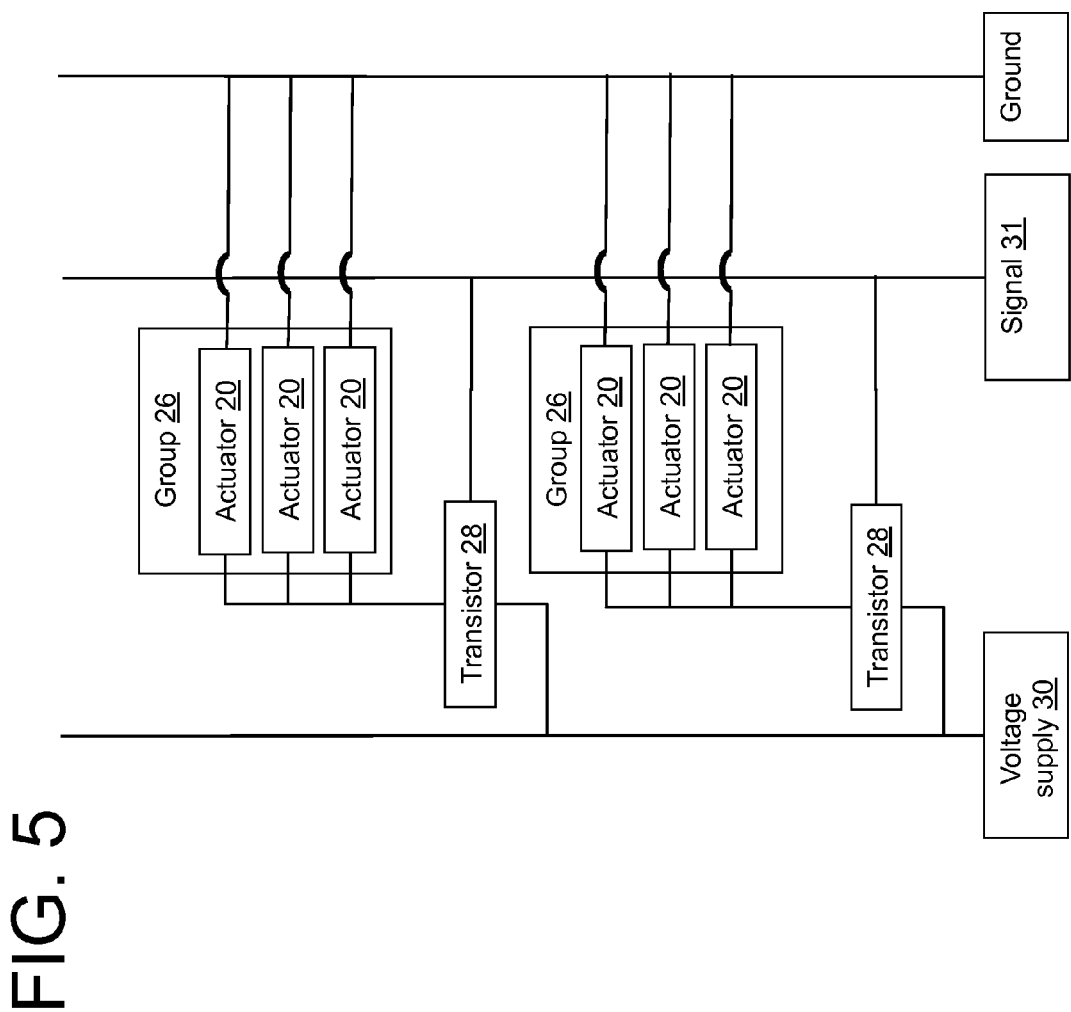

ACTUATABLE VISUAL INSPECTION DEVICE

BACKGROUND OF THE INVENTION

The invention relates generally to a device for inspection of machines and systems having an external casing concealing internal passage and/or cavities. More particularly, the invention relates to an actuated visual inspection device.

Many types of industrial machines such as, e.g., gas turbines, include critical components which are encased within an external casing or shell. During the life cycle of a machine, these critical components require inspection in order to maximize the lifespan of the parts and the machine as a whole. Traditionally, access to components for inspection, repair or maintenance has been obtained by removing the casing and disassembling the machine as needed. This process can be technically difficult, time consuming, labor intensive, and expensive. Disassembly of the machine incurs costs both in labor required to disassemble the machine and casing, and in non-productive down time for the machine.

In order to avoid disassembly, borescopes have been used to remotely visualize otherwise inaccessible components. Borescopes are typically fed by hand, and navigate using a controllable tip. The bodies of borescopes are typically flexible, but non-actuated. Maneuvering through tight spaces and along complex paths is difficult, and requires the inclusion of multiple ports along the machine, to limit the distance a borescope must traverse.

BRIEF DESCRIPTION OF THE INVENTION

Described herein is an actuatable visual inspection device for visualizing internal components of, e.g., a machine having an external casing.

A first aspect of the disclosure provides a visual inspection device comprising a tube having a lumen disposed therein, and a visual inspection tool disposed at a distal end of the tube. A plurality of actuators is disposed along an axial extent of an exterior of the tube; and a locomotor is disposed on an exterior of the tube for propelling the visual inspection device along a surface of passageway or cavity. A locator for tracking a location of the visual inspection tool is further disposed on the visual inspection device.

A second aspect of the disclosure provides a visual inspection device comprising a visual inspection tool in the form of a borescope, and a tube having a lumen disposed therein. The borescope is disposed on a distal end of the tube. A plurality of groups of actuators are disposed along an axial extent of an exterior of the tube; and a locomotor is disposed on an exterior of the tube. At least one locator for tracking a location of the visual inspection tool is provided on the visual inspection device. A computing device in electrical signal communication with the at least one locator, the visual inspection tool, and the plurality of groups of actuators is also provided, the computing device being configured to perform rendering a three-dimensional model of an environment into which the visual inspection device is inserted; calibrating a location of the visual inspection device relative to the model; processing audiovisual data received from the visual inspection tool, and generating a texture layer on the three-dimensional model, wherein the texture layer represents the audiovisual data received from the visual inspection tool.

These and other aspects, advantages and salient features of the invention will become apparent from the following detailed description, which, when taken in conjunction with the annexed drawings, where like parts are designated by like reference characters throughout the drawings, disclose embodiments of the invention.

BRIEF DESCRIPTION OF THE DRAWINGS

FIG. 1 shows a perspective illustration of a visual inspection device according to an embodiment of the invention.

FIG. 2 shows a cross sectional view of the visual inspection device shown in FIG. 1, according to an embodiment of the invention.

FIGS. 3 and 4 depict top views of a portion of a visual inspection device in its un-actuated and actuated states respectively, in accordance with an embodiment of the invention.

FIG. 5 depicts a schematic diagram of a portion of a circuit in accordance with embodiments of the invention.

DETAILED DESCRIPTION OF THE INVENTION

Figure 7:
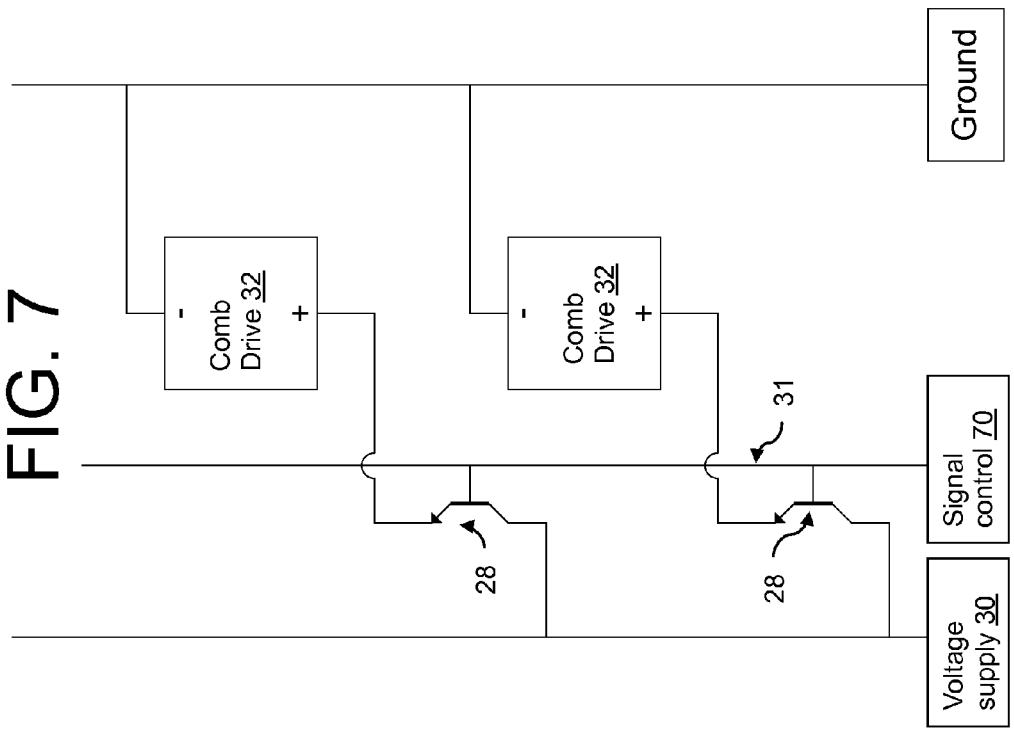
FIG. 7 depicts a schematic diagram of a portion of a circuit in accordance with embodiments of the invention.

At least one embodiment of the present invention is described below in reference to its application in connection with a visual inspection device useful in the visual inspection of a machine or complex system. Although embodiments of the invention are illustrated and described relative to inspection of a turbomachine in the form of a gas turbine, it is understood that the teachings are equally applicable to other turbomachines and electric machines including, but not limited to, other types of turbines including steam turbines, wind turbines, wind turbine gear boxes, generators, aircraft engines, reciprocating engines, appliances, accessory bases, locomotive power train machines, healthcare machines such as MRI, CT, and x-ray machines, hydro turbine machines, electric motors, pumps, transformers, switchgears, and generator excitation equipment. Further, at least one embodiment of the present invention is described below in reference to a nominal size and including a set of nominal dimensions. However, it should be apparent to those skilled in the art that the present invention is likewise applicable to any suitable turbomachine and/or electric machine having an outer casing, or other complex system in which visualization is advantageous. Further, it should be apparent to those skilled in the art that the present invention is likewise applicable to various scales of the nominal size and/or nominal dimensions.

As indicated above, aspects of the invention provide a visual inspection device 10 for visually inspecting passages and cavities that are inaccessible from an exterior of a complex machine and/or system. As shown in FIG. 1, visual inspection device 10 includes visual inspection tool 12, and a tube 14 having a lumen 16 disposed therein. Visual inspection tool 12 may include, e.g., a borescope, and can be disposed at a distal end 18 of tube 14. A plurality of actuators 20 and a locomotor 22 are disposed along an axial extent of the exterior of tube 14.

As shown in FIGS. 1-2, in one embodiment, the plurality of actuators may be arranged in rows extending along an axial extent of tube 14. The number of rows may be two or more than two, and may more particularly be between three and six, which may be distanced substantially equidistantly about the circumference of tube 14. Actuation of a particular group 26 of actuators 20 may cause tube 14 to bend as shown in FIG. 4, and as will be explained further below. Greater numbers of actuators 20 will provide finer grain control over the movement of visual inspection device 10.

With reference to FIG. 3, individual actuators 20 may be arranged into groups 26 which may be actuated collectively. Regardless of whether actuators 20 are actuated individually or in groups 26, the actuation may be accomplished through the use of a transistor 28, which triggers the actuation. Transistors 28 may be arranged serially, as shown in the schematic circuit diagram of FIG. 5. Each transistor 28 may have a source and a gate leg connected to a common voltage supply 30 and a signal path 31. A digital signal of binary code can then be transmitted along signal path 31. Each transistor 28 is assigned a unique binary code, so that only the corresponding transistor 28 to the code transmitted will respond by opening or closing the transistor gate, triggering an actuator 20 or group of actuators 26 (FIG. 5). Various embodiments may include various types of actuators 20, each of which acts to lengthen or shorten a portion of the circumference of tube 14, imparting a bending moment to a specific section of tube 14 as shown in FIG. 4. Because actuators 20 run the axial extent of tube 14, as shown in FIG. 1, the actuation of different actuators 20 or groups 26 of actuators 20 at different points along the axial extent of tube 14 allows for multiple different bends and movements in tube 14 simultaneously, allowing it to navigate complex pathways.

Referring back to FIG. 1, locomotor 22 works in concert with actuators 20 to accomplish locomotion through passageways by propelling visual inspection device 10 along a surface of the passageway at angles established by actuators 20. In one embodiment, locomotors 22 may include sets of motorized rollers on an exterior of the device under inspection. In such an embodiment, tube 14 may be pushed into the cavity or pathway from the exterior. Actuators 20 would provide the proper bend(s) in tube 14, allowing the hose to navigate a complex path as it is propelled by locomotor 22.

Figure 6:
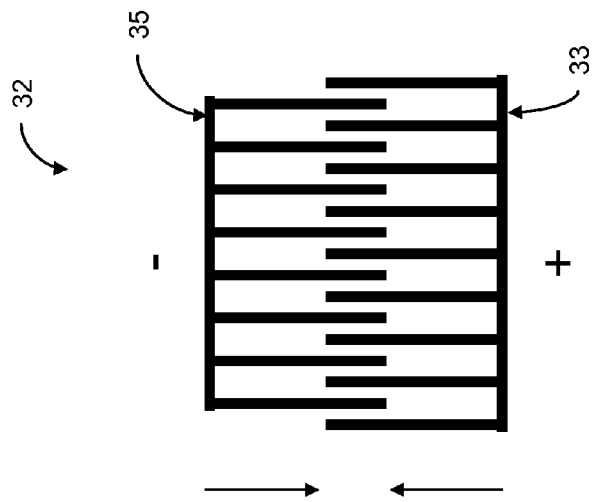
FIG. 6 depicts a schematic diagram of an electrostatic comb drive actuator in accordance with embodiments of the invention.

With reference to FIG. 6, in one embodiment, actuator 20 (FIG. 5) may be in the form of a micro-electro-mechanical systems (MEMS) electrostatic comb drive 32. The electrostatic comb drive 32 operates by including a first comb 33 connected to a positive electrical source, and a second comb 35 connected to a negative electrical source. When current is passed through the first and second combs 33, 35, the combs 33, 35 attract one another. First and second combs 33, 35 are coupled to tube 14, so that when they attract, they pull on tube 14, causing the portion of tube 14 at that point on the circumference and axial extent to contract. A plurality of pairs of combs 33, 35 may be arranged in rows along the axial extent of tube 14. For example, rows may be made of groups of approximately 100 pairs of combs 33, arranged over a linear 2.54 cm (1 inch) of axial extension of tube 14. In various embodiments combs 33, 35 may be arranged in two or more longitudinal rows running along the tube 14, substantially equidistant from one another. In some embodiments, combs 33, 35 may particularly be arranged in three to six longitudinal rows running along the tube 14. By passing current through one or both of first and second combs 33, 35, the combs can attract or repel one another, causing a specific section of tube 14 to contract or expand. As shown in the schematic circuit diagram of FIG. 7, each transistor 28 may have a source and a gate leg connected to a common voltage supply 30 and a signal path 31. A digital signal of binary code can then be transmitted along signal path 31. Only the corresponding transistor 28 to the code transmitted will respond by opening or closing the transistor gate, triggering the flow of current through comb drive 32.

Figure 9:
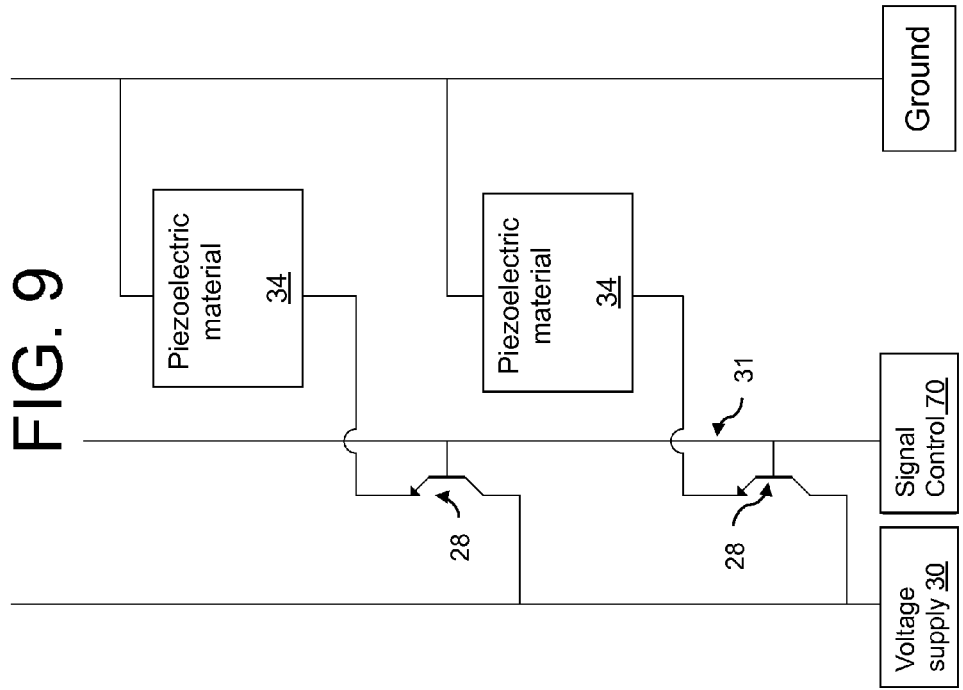
FIG. 9 depicts a schematic diagram of a portion of a circuit in accordance with embodiments of the invention.
Figure 8:
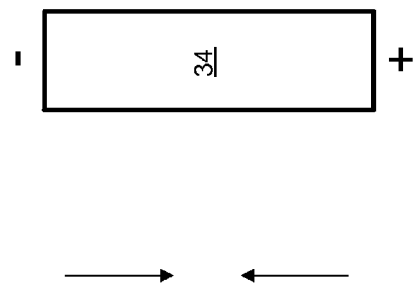
FIG. 8 depicts a schematic diagram of a piezoelectric actuator in accordance with embodiments of the invention.

With reference to FIG. 8, in one embodiment, actuator 20 (FIG. 5) may be in the form of a piezoelectric material member 34. The piezoelectric material member 34 is affixed to tube 14 in a fashion similar to that described relative to the electrostatic comb drives 32. The piezoelectric material members 34 may be affixed to an outer surface of tube 14 in axially extending rows. Voltage is applied in a similar fashion, triggered by transistors 28, causing a change in length of the piezoelectric material member 34. A first voltage may be applied to cause the piezoelectric material member 34 to contract or shorten, causing tube 14 to bend around that section, and a second voltage may be applied to cause the piezoelectric material member 34 to expand, causing tube 14 to bend away from the piezoelectric material member 34. As shown in the schematic circuit diagram of FIG. 9, each transistor 28 may have a source and a gate leg connected to a common voltage supply 30 and a signal path 31. A digital signal of binary code can then be transmitted along signal path 31. Only the corresponding transistor 28 to the code transmitted will respond by opening or closing the transistor gate, triggering the flow of current through piezoelectric material member 34.

Figure 11:
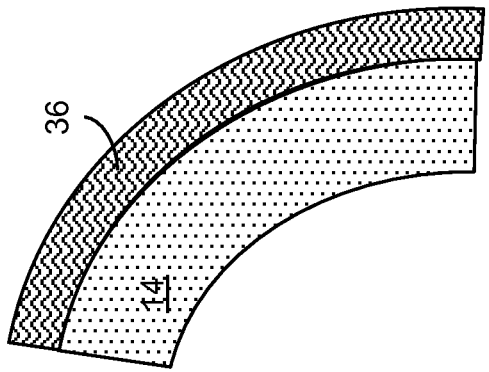
FIGS. 10 and 11 depict top views of a portion of a visual inspection device in its un-actuated and actuated states respectively in accordance with embodiments of the invention.
Figure 10:
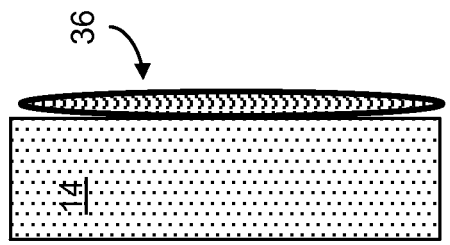

With reference to FIGS. 10-11, in another embodiment, actuator 20 (FIG. 5) may be in the form of an expandable bladder 36. The expandable bladder 36 operates either pneumatically or hydraulically, i.e., it may be filled with either air or fluid. FIG. 10 shows bladder 36 in its un-actuated condition, while FIG. 11 shows bladder 36 in its actuated, or pressurized condition. Bladders 36 may be affixed to tube 14 in a fashion similar to that described relative to the electrostatic comb drives 32, i.e., bladders 36 may be affixed to an outer surface of tube 14 in axially extending rows. Pressurizing bladder 36 causes the underlying section of tube 14 to stretch, resulting in a bend as shown in FIG. 11.

Figure 12:
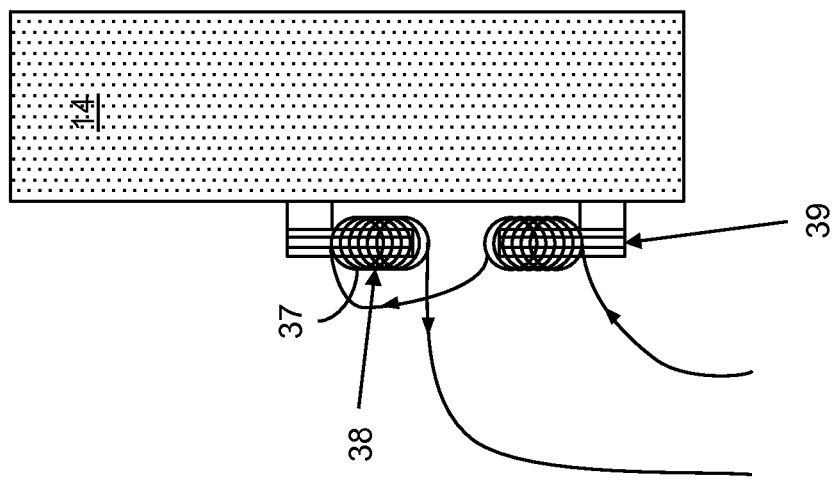
FIG. 12 depicts a top view of a solenoid actuator in accordance with embodiments of the invention.

With reference to FIG. 12, in another embodiment, actuator 20 may be a solenoid 38. The solenoid 38 may include a magnetic bar 39 affixed to tube 14, having a coil 37 disposed about the magnetic bar 39. Current may be run through coil 37, inducing a magnetic force that effects a squeezing action on tube 14.

Figure 14:
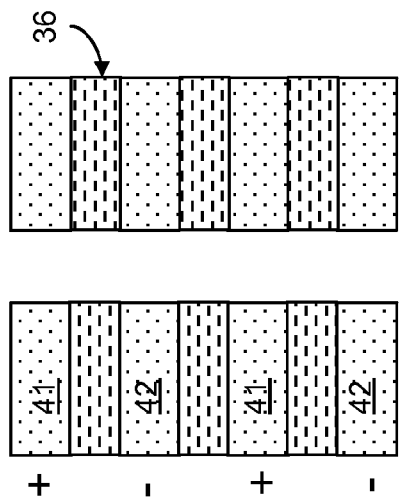
FIGS. 14 and 15 depict top views of a portion of a visual inspection device in its un-actuated and actuated states respectively in accordance with embodiments of the invention.
Figure 15:
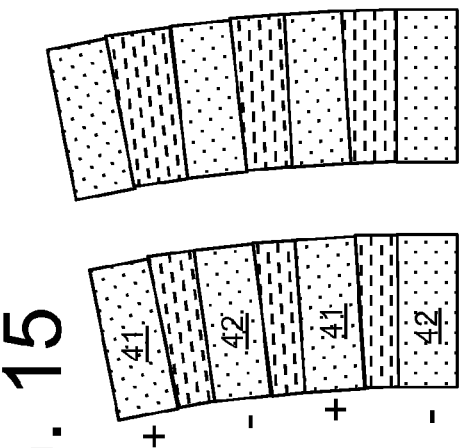
Figure 13:
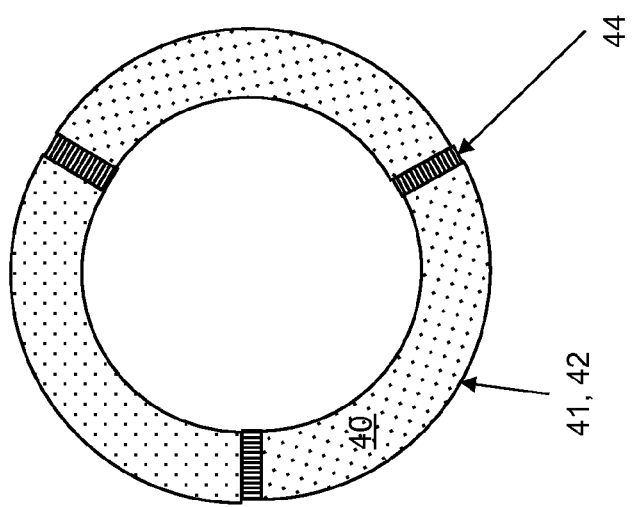
FIG. 13 depicts a cross sectional view of a portion of a visual inspection device in accordance with embodiments of the invention.

With reference to FIGS. 13-15, in another embodiment, actuator 20 may be a stack of electromagnetically attracting plates 40 (FIG. 13) having an annular shape similar to washers. The plates 40 operate by means of electrostatic attraction. Tube 14 may be made up of alternating plates 40 (FIG. 13) of positively 41 and negatively charged 42 materials (FIGS. 14-15), separated by layers of compressible insulating material 43 there between. Plates 40, whether they are positively 41 or negatively 42 charged, may be divided into two or more arcuate segments (three shown in FIG. 13), with sections of insulating material 44, such as plastic, dividing the arcuate segments. In some embodiments, plates 40 may particularly be divided into three to six arcuate segments. Actuation, in the form of applying a voltage across two adjacent plates, causes them to attract and compress insulating material 43 as shown in FIG. 15. Insulating material 43 prevents an electrical short between adjacent plates 41, 42. With reference to FIG. 13, each arcuate segment of plates 41, 42 may be actuated independently of the other arcuate segments, causing a bend in tube 14 in given direction as shown in FIG. 15.

Referring back to FIG. 1, visual inspection device 10 may further include a locator 24 for tracking a location of visual inspection device 10. In various embodiments, locator 24 may take one of a number of forms. Locator 24 may be disposed on visual inspection tool 12 in some embodiments. In other embodiments, a plurality of locators 24 may be disposed along an axial extent of visual inspection device 10.

In one embodiment, locator 24 may be, for example, a optical fiber device including an Optical Frequency Domain Reflectometer. In such an embodiment, a fiber optic cable runs along an axial length of the interior of lumen 16 of tube 14. The fiber optic cable may include hundreds or thousands of fiber Bragg gratings (FBG), each of which acts as a strain gage. Each FBG is constructed in a short segment of optical fiber that reflects particular wavelengths of light and transmits all other wavelengths of light. This is achieved by creating a periodic variation in the refractive index of the fiber core, which generates a wavelength-specific dielectric mirror. Light may be shined in one end of the fiber optic cable, and locator 24 may analyze the light reflected, and use this information to read each strain gage and determine the shape of the optical fiber, and therefore the shape of tube 14. Locator 24 may then communicate this information to computing device 50 as discussed further below.

In another embodiment, locator 24 may be composed of a plurality of strain gauges. By measuring and recording strain along length of tube 14 at, for example, 120 degree intervals around the circumference of tube 14 at a plurality of points along the axial extent of tube 14, this data can be used to build a model of the location of the entire tube 14. Electrostatic comb drive 32 (FIGS. 6-7) and piezoelectric material member 34 (FIGS. 8-9) can be used in this way, not only to impart bending moment to tube 14, but also to calculate the position of tube 14. This can be done by characterizing, through experiments, the displacement of actuator 20 as a function of applied voltage. Once this is known, the displacement can be inferred from the voltage applied to actuator 20. Accordingly, in some embodiments, locator 24 and actuators 20 may be a single device performing both functions.

In another embodiment, locator 24 may include an emitter disposed on visual inspection tool 12 which emits an electromagnetic signal for triangulation. The emitter may be, e.g., a radio frequency identification (RFID) tag or other radio frequency transmitter. The frequency used should be one which can be received through an exterior casing of the machine or system being inspected. A number of antennas may be disposed outside the casing of the system being inspected, allowing a position of the visual inspection tool 12 to be determined.

In still another embodiment, locator 24 may include an inertial guidance system, including at least one accelerometer and/or gyroscope. Once an initial position is determined, the measurements taken from an accelerometer and a gyroscope disposed on visual inspection tool 12 can identify the present location of visual inspection tool 12 as calculated based on the cumulative effect of all accelerations and orientation changes since the original position.

Figure 16:
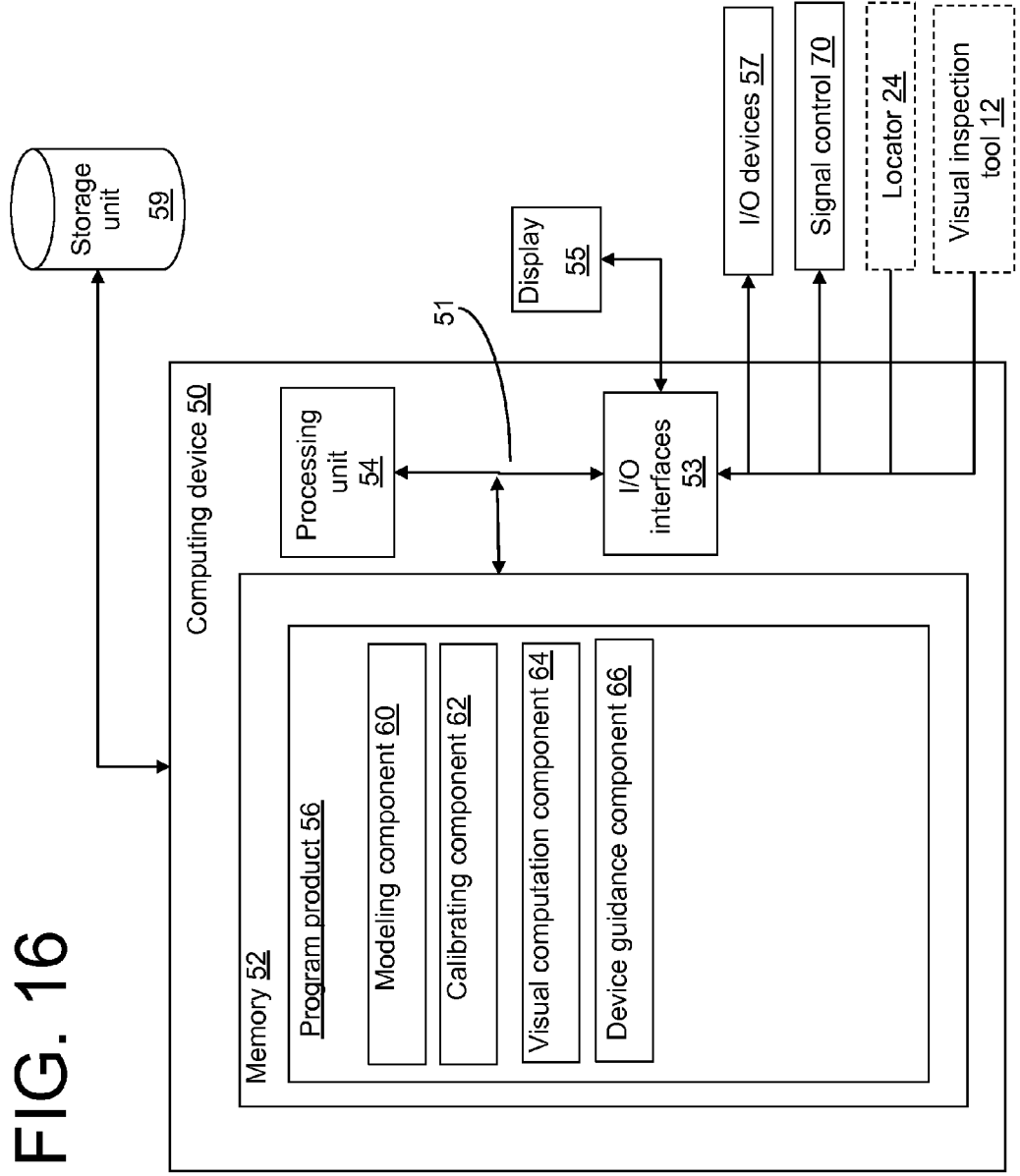
FIG. 16 depicts a schematic diagram of a computing device in accordance with embodiments of the invention.

With reference to FIG. 16, a schematic illustration is provided of an environment according to various embodiments including a computing device in electrical signal communication with several of the features of visual inspection device 10, as described further below.

As shown in FIG. 16, computing device 50 includes a processing unit 54, a memory 52, input/output (I/O) interfaces 53 operably connected to one another by pathway 51, which provides a communications link between each of the components in computing device 50. Further, computing device 50 is shown in communication with display 55, external I/O devices/resources 57, and storage unit 59, which may display, manipulate, and store respectively, data obtained by visual inspection device 10. I/O devices 57 can comprise one or more human I/O devices, such as a mouse, keyboard, joystick, or other selection device, which enable a human user to interact with computing device 50 and/or one or more communications devices to enable a device user to communicate with computing device 50 using any type of communications link.

In general, processing unit 54 executes computer program product (or, program) 56 which provides the functions of computing device 50. Program product 56 may include a plurality of components, including a modeling component 60, a calibrating component 62, a visual computation component 64, and a device guidance component 66, which are stored in memory 52 and/or storage unit 59, and perform the functions and/or steps of the present invention as described herein. Memory 52 and/or storage unit 59 can comprise any combination of various types of computer readable data storage media that reside at one or more physical locations. To this extent, storage unit 59 could include one or more storage devices, such as a magnetic disk drive or an optical disk drive. Still further, it is understood that one or more additional components not shown in FIG. 16 can be included in computing device 50, including analysis of the data captured by visual inspection device 10 and transmitted in real time to computing device 50. Additionally, in some embodiments one or more external devices 57, display 55, and/or storage unit 59 could be contained within computing device 50, rather than externally as shown.

Computing device 50 can comprise one or more general purpose computing articles of manufacture capable of executing program code, such as program 56, installed thereon. As used herein, it is understood that "program code" means any collection of instructions, in any language, code or notation, that cause a computing device having an information processing capability to perform a particular action either directly or after any combination of the following: (a) conversion to another language, code or notation; (b) reproduction in a different material form; and/or (c) decompression. To this extent, program 56 can be embodied as any combination of system software and/or application software.

Further, program 56 can be implemented using a set of components 60, 62, 64, 66. In this case, components 60, 62, 64, 66 can enable computing device 50 to perform a set of tasks used by program 56, and can be separately developed and/or implemented apart from other portions of program 56. As used herein, the term "component" means any configuration of hardware, with or without software, which implements the functionality described in conjunction therewith using any solution, while the term "component" means program code that enables a computing device 50 to implement the actions described in conjunction therewith using any solution. When fixed in memory 52 or storage unit 59 of a computing device 50 that includes a processing unit 54, a component is a substantial portion of a component that implements the actions. Regardless, it is understood that two or more components, components, and/or systems may share some/all of their respective hardware and/or software. Further, it is understood that some of the functionality discussed herein may not be implemented or additional functionality may be included as part of computing device 50.

When computing device 50 comprises multiple computing devices, each computing device can have only a portion of program 56 fixed thereon (e.g., one or more components 60, 62, 64, 66). However, it is understood that computing device 50 and program 56 are only representative of various possible equivalent computer systems that may perform a process described herein. To this extent, in other embodiments, the functionality provided by computing device 50 and program 56 can be at least partially implemented by one or more computing devices that include any combination of general and/or specific purpose hardware with or without program code. In each embodiment, the hardware and program code, if included, can be created using standard engineering and programming techniques, respectively.

Regardless, when computing device 50 includes multiple computing devices, the computing devices can communicate over any type of communications link. Further, while performing a process described herein, computing device 50 can communicate with one or more other computer systems using any type of communications link. In either case, the communications link can comprise any combination of various types of wired and/or wireless links; comprise any combination of one or more types of networks; and/or utilize any combination of various types of transmission techniques and protocols.

As noted, computing device 50 may be in signal communication with several of the features of visual inspection device 10. Such communication may be either wired, via wires 72 passing through lumen 16 of tube 14, or wireless.

In particular, computing device 50 may be in communication with signal control device 70 (FIGS. 7, 9, 16), allowing computing device 50, or an end user via computing device 50, to control the actuation of groups 26 of actuators 20 (FIG. 3), and therefore the movement of visual inspection tool 10. Signal control device 70 may further transmit signals controlling locomotor 22 (FIG. 1).

As noted, computing device 50 includes a modeling component 60 for rendering a three-dimensional model of an environment into which the visual inspection device 10 is inserted. In various embodiments, the environment may include, for example, an interior of machine or complex system.

Computing device 50 may further be in communication with locator 24, such that locator 24 transmits, and computing device 50 receives, a signal indicating a present location of locator 24 and therefore all or part of visual inspection device 10. Computing device 50 may include a calibrating component 62, for calibrating an initial location of visual inspection device 10 relative to the model rendered by modeling component 60 and the physical environment into which visual inspection device 10 is inserted. Calibrating component 62 uses data received from locator 24 to locate visual inspection device 10 in the model.

Computing device 50 may further be in communication with visual inspection tool 12, such that visual inspection tool 12 transmits, and computing device 50 receives, a signal providing audiovisual data such as an image or video feed from visual inspection tool 12.

Visual computation component 64, part of program product 56, may be provided for processing audiovisual data received from the visual inspection tool. Visual computation component 64 may then use the audiovisual data to generate a texture layer on the three-dimensional model generated by modeling component 60. The texture layer represents the audiovisual data received from the visual inspection tool, and may be displayed in the form of a series of surfaces. The model generated by modeling component 60, including textures layered onto the model by visual computation component 64, may be displayed to an end user on a display 55. This model may be used to determine the location, size, and severity of surface imperfections or other features of interest on an interior passage or cavity in the environment.

Device guidance component 66 may further be provided as part of program product 56 for automatically guiding visual inspection device 10 through the environment in which it is inserted. Device guidance component 66 may determine, based on the location of visual inspection device 10 and the three-dimensional model, and initiate the movements, including actuation and locomotion, necessary to advance visual inspection device 10 in a pre-selected desired direction, e.g., toward an area of interest or to withdraw device 10 from the environment.

Technical effects of the various embodiments of the present invention include providing a visual inspection device 10 capable of navigating complex pathways including a plurality of direction changes to reach an area of interest. Visual inspection device 10 may be used to inspect interior surfaces of machines, such as gas turbines and other turbomachines, and other complex systems. Further embodiments provide additional capabilities, including generating and displaying a model of the interior of the machine or system, including locating the visual inspection device on the model, and displaying images from the visual inspection device as a texture overlaid on the model.

As used herein, the terms "first," "second," and the like, do not denote any order, quantity, or importance, but rather are used to distinguish one element from another, and the terms "a" and "an" herein do not denote a limitation of quantity, but rather denote the presence of at least one of the referenced item. The modifier "about" used in connection with a quantity is inclusive of the stated value and has the meaning dictated by the context (e.g., includes the degree of error associated with measurement of the particular quantity). The suffix "(s)" as used herein is intended to include both the singular and the plural of the term that it modifies, thereby including one or more of that term (e.g., the metal(s) includes one or more metals). Ranges disclosed herein are inclusive and independently combinable (e.g., ranges of "up to about 25 mm, or, more specifically, about 5 mm to about 20 mm," is inclusive of the endpoints and all intermediate values of the ranges of "about 5 mm to about 25 mm," etc.).

While various embodiments are described herein, it will be appreciated from the specification that various combinations of elements, variations or improvements therein may be made by those skilled in the art, and are within the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A visual inspection device comprising:
 a tube having a lumen disposed therein;
 a visual inspection tool disposed at a distal end of the tube;

a plurality of actuators arranged substantially continuously along an axial extent of an exterior of the tube;
a locomotor disposed on an exterior of the tube; and
at least one locator for tracking a location of the visual inspection tool; and
a computing device in electrical signal communication with the at least one locator and the visual inspection tool, the computing device being configured to receive a signal from each of the locator and the visual inspection tool,
wherein the computing device is further configured to perform;
rendering a three-dimensional model of an environment into which the visual inspection device is inserted;
calibrating a location of the visual inspection device relative to the model; and
automatically determining and initiating a movement of the visual inspection device toward a pre-selected location, based on the location and the three-dimensional model, wherein the movement includes at least one of an actuation and a locomotion.

2. The visual inspection device of claim 1, wherein the visual inspection tool further comprises a borescope.

3. The visual inspection device of claim 1, wherein the plurality of actuators is grouped into a plurality of groups of actuators.

4. The visual inspection device of claim 3, wherein the plurality of groups of actuators further comprises two or more groups of actuators disposed substantially equidistantly from each other group of actuators about a circumference of the tube.

5. The visual inspection device of claim 3, wherein each of the plurality of groups of actuators is triggered by an associated transistor.

6. The visual inspection device of claim 5, wherein the transistors associated with each of the groups of actuators are arranged in serial.

7. The visual inspection device of claim 5, wherein each group of actuators is assigned a unique binary code, and
wherein each transistor is electrically connected to a common voltage supply, such that a transmission of a digital signal of binary code along the voltage supply operates a gate in a desired transistor.

8. The visual inspection device of claim 5, further comprising
a computing device in electrical signal communication with the transistor associated with each of the groups of actuators,
wherein the computing device is further configured to transmit a signal to the transistor.

9. The visual inspection device of claim 1, wherein each actuator in each of the plurality of groups of actuators further comprises one of the group consisting of:
an electrostatic comb drive,
a piezoelectric material member,
an expandable bladder,
a solenoid, and
a plurality of electromagnetically attracting plates.

10. The visual inspection device of claim 1, wherein the locator further comprises one of the group consisting of:
a fiber optic device disposed on the visual inspection tool,
an electromagnetic signal emitter disposed on the visual inspection tool, wherein the emitter emits an electromagnetic signal for triangulation,
a plurality of strain gauges disposed on the tube, and
an inertial guidance system disposed on the visual inspection tool.

11. The visual inspection device of claim 1, wherein the computing device is further configured to perform:
processing audiovisual data received from the visual inspection tool, and generating a texture layer on the three-dimensional model, wherein the texture layer represents the audiovisual data received from the visual inspection tool.

12. A visual inspection device comprising:
a tube having a lumen disposed therein,
a visual inspection tool including a borescope, the visual inspection tool being disposed at a distal end of the tube;
a plurality of groups of actuators, each group of actuators including a plurality of actuators, disposed along an axial extent of an exterior of the tube;
a locomotor disposed on an exterior of the tube;
at least one locator for tracking a location of the visual inspection device; and
a computing device in electrical signal communication with the at least one locator, the visual inspection tool, and the plurality of groups of actuators, the computing device being configured to perform:
rendering a three-dimensional model of an environment into which the visual inspection device is inserted;
calibrating a location of the visual inspection device relative to the model; and
processing audiovisual data received from the visual inspection tool, and generating a texture layer on the three-dimensional model, wherein the texture layer represents the audiovisual data received from the visual inspection tool.

13. The visual inspection device of claim 12, wherein the plurality of groups of actuators further comprises two or more groups of actuators disposed substantially equidistantly from each other group of actuators about a circumference of the tube.

14. The visual inspection device of claim 13,
wherein each of the groups of actuators is triggered by an associated transistor,
wherein the transistors associated with each of the groups of actuators are arranged in serial,
wherein each group of actuators in the plurality of groups is assigned a unique binary code, and
wherein each transistor is electrically connected to a common voltage supply, such that a transmission of a digital signal of binary code along the voltage supply operates a gate in a desired transistor.

15. The visual inspection device of claim 12, wherein each actuator in the plurality of actuators further comprises an electrostatic comb drive.

16. The visual inspection device of claim 12, wherein each actuator in the plurality of actuators further comprises a piezoelectric material member.

17. The visual inspection device of claim 12, wherein the locator further comprises one of the group consisting of:
a fiber optic device disposed on the visual inspection tool;
an electromagnetic signal emitter disposed on the visual inspection tool, wherein the emitter emits an electromagnetic signal for triangulation;
a plurality of strain gauges disposed on the tube; and
an inertial guidance system disposed on the visual inspection tool.

18. The visual inspection device of claim 12, wherein the computing device is further configured to perform:
automatically determining and initiating a movement of the visual inspection device toward a pre-selected location, based on the location and the three-dimensional model, wherein the movement includes at least one of an actuation and a locomotion.

* * * * *